United States Patent [19]

Waite

[11] Patent Number: 4,848,333
[45] Date of Patent: Jul. 18, 1989

[54] OXYGEN DILUTION APPARATUS

[75] Inventor: Richard B. Waite, Castle Cove, Australia

[73] Assignee: Waite & Co. Pty. Limited, New South Wales, Australia

[21] Appl. No.: 127,362

[22] Filed: Dec. 2, 1987

[30] Foreign Application Priority Data

Dec. 9, 1986 [AU] Australia ............................. PH9398

[51] Int. Cl.⁴ ............................................. A62B 7/00
[52] U.S. Cl. .......................... 128/205.11; 128/205.24
[58] Field of Search ...................... 128/205.11, 205.24; 251/121, 122, 205, 208, 341, 351, 108; 137/892, 898; 62/13

[56] References Cited

U.S. PATENT DOCUMENTS

| | | | |
|---|---|---|---|
| 755,332 | 3/1904 | Thiele | 251/108 |
| 1,596,913 | 8/1926 | Wilson | 251/108 |
| 1,786,357 | 12/1930 | Miller | 137/892 |
| 1,929,973 | 10/1933 | Haley | 251/122 |
| 2,655,992 | 10/1953 | Le Renard | 137/892 |
| 3,236,059 | 2/1966 | Bernstein | 62/13 |
| 3,526,239 | 9/1970 | Oroza | 137/81.1 |
| 3,526,240 | 9/1970 | Oroza | 137/81.1 |
| 3,526,241 | 9/1970 | Veit | 128/204.29 |
| 3,830,257 | 8/1974 | Metivier | 128/205.11 |
| 3,881,480 | 5/1975 | Lafourcade | 128/204.25 |
| 3,886,972 | 6/1975 | Scott et al. | 137/897 |
| 3,913,607 | 10/1975 | Price | 128/205.11 |
| 3,977,432 | 8/1976 | Vidal | 128/205.11 |
| 4,036,253 | 7/1977 | Fegan et al. | 137/892 |
| 4,072,148 | 2/1978 | Munson et al. | 128/205.11 |
| 4,121,580 | 10/1978 | Fabish | 128/205.11 |
| 4,612,926 | 9/1986 | Boiarski et al. | 128/205.11 |
| 4,615,352 | 10/1986 | Gibot | 137/892 |

FOREIGN PATENT DOCUMENTS

| | | |
|---|---|---|
| 103816 | 12/1917 | United Kingdom . |
| 1039816 | 8/1966 | United Kingdom . |
| 1420215 | 1/1976 | United Kingdom . |
| 2133714 | 8/1984 | United Kingdom . |

Primary Examiner—Edgar S. Burr
Assistant Examiner—Aaron J. Lewis
Attorney, Agent, or Firm—Sixbey, Friedman, Leedom & Ferguson

[57] ABSTRACT

This invention concerns oxygen dilution apparatus of the kind used when providing inhalation therapy, and a method of adjusting the air dilution of an oxygen supply for an inhalation mask. The invention involves a mixing valve (1) connected into the oxygen line supplying a face-mask. The valve body comprises an orifice (14) communicating with the atmosphere. The ratio of air to oxygen delivered to the mask is controlled by operating the valve to change the cross sectional area of the oxygen inlet port. Preferably this is done by rotating two parts (2,20) of the valve with respect to each other, which action causes the insertion or withdrawal of a stem (23) of varying cross-section in an aperture (19) of constant cross-section. The invention has the advantage that oxygen dilution is controlled by a geared-down motion which allows the two parts of the valve body to be moved in a reliable and foolproof manner between positions which result in different proportions of oxygen and air being delivered. The invention also has the advantage that accidental or inadvertent adjustment of the ratio is very unlikely.

14 Claims, 2 Drawing Sheets

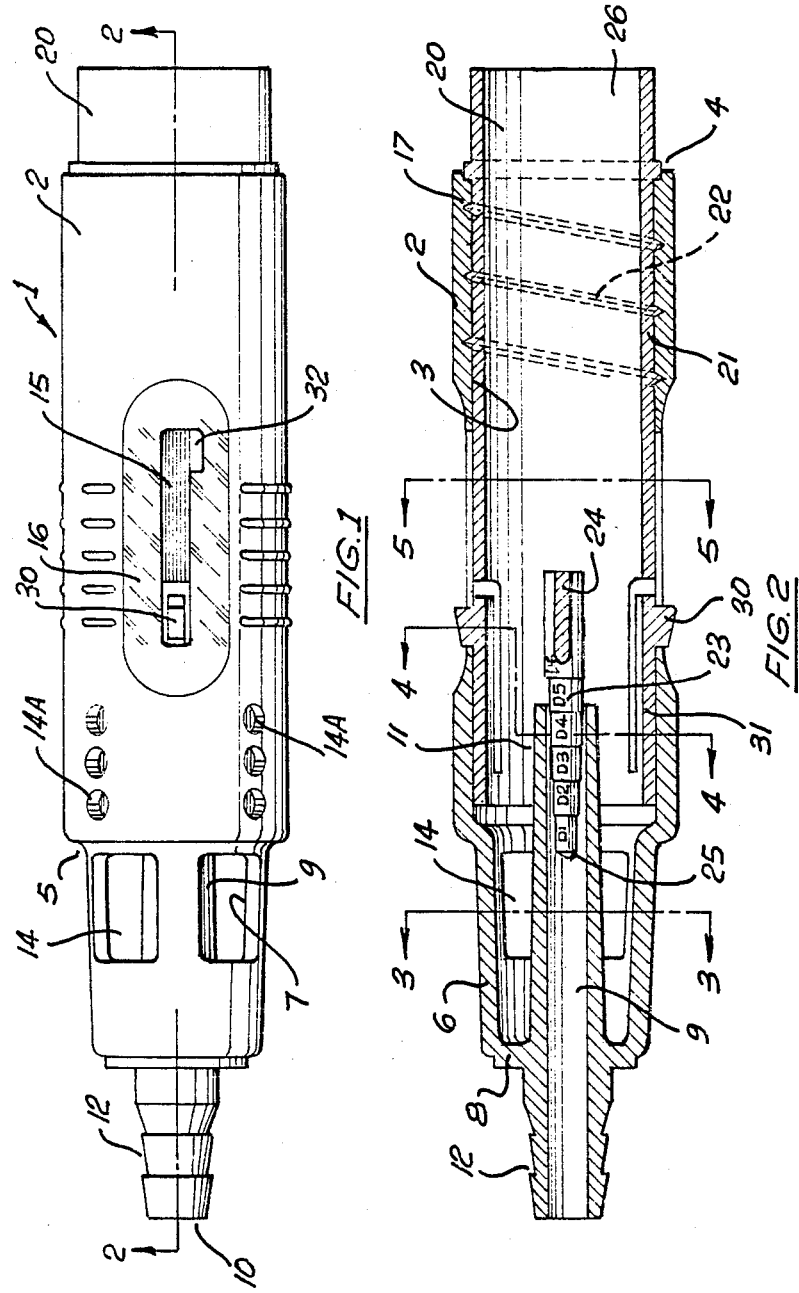

OXYGEN DILUTION APPARATUS

This invention relates to oxygen dilution apparatus of the kind used when providing inhalation therapy.

Oxygen dilution apparatus such as described in U.S. Pat. No. 3,913,607 takes a flow of oxygen from a regulated flow rate supply and passes the oxygen into a chamber through a nozzle orifice. The chamber is in communication with atmosphere. As oxygen flows from the nozzle into the chamber air surrounding the oxygen stream becomes entrained in the stream and fresh air is drawn into the chamber through a slot in the chamber wall. The aperture of the slot is adjustable whereby the ratio of air admitted to the chamber and combined with the oxygen stream may be adjusted to some extent. The mixture of air and oxygen is conducted from a chamber outlet port to an inhalation mask. The slot aperture is adjusted by rotation of one tubular chamber part ("selector") having a window with respect to another tubular chamber part ("barrel") having an overlapping window, the area of overlap determining the aperture area of the slot through which air is admitted for mixing.

Prior oxygen dilution apparatus of the above kind suffers from a number of disadvantages.

One selector is required to supply the dilution range of from 24-30% air to oxygen while a second selector with a larger jet nozzle and a smaller air aperture slot is required for ranges 35-50%. Thus 2 selectors are required to cover the full desired range, necessitating storage of the unused part and general inconvenience. Furthermore, it is advisable for the oxygen flow rate to be adjusted as well as the air aperture. For example a flow rate of 3 liters per minute ("LPM") may be recommended for use with selected apertures A or B to give respectively 24% or 26% dilution while 6 LPM may be recommended for use when apertures C, D are selected to give respectively 28% or 30% dilution. There is thus introduced opportunity for error in mix-combining an air admission aperture with a given oxygen flow rate or vice versa.

Furthermore, if too small an air admission slot is used, there is a risk that if a patient's peak inspiratory flow rate exceeds the delivery rate of mixed gases, the patient will draw additional air through the slot resulting in greater than anticipated dilution.

Another disadvantage of prior art is that a step change of from say 24% to 26% dilution may be brought about by a very small rotation of the "selector" part. Although click stops have been provided, these do not have a sufficiently positive action and the dilution level may easily be mis-selected as a result of error or may become incorrectly set by being accidentally bumped.

A further disadvantage of prior art is that tolerances on the pinhole orifice of the nozzle are necessarily critical if correct dilutions are to be obtained, thus complicating manufacture as well as care and use of the apparatus.

An object of the present invention is to provide oxygen dilution apparatus which in preferred embodiments avoids or ameliorates some of the above described disadvantages of prior art.

According to one aspect the invention consists in a method for adjusting the air dilution of an oxygen supply for an inhalation mask, said method comprising the steps of:

admitting oxygen into a chamber through an orifice,
admitting air into the chamber through an inlet,
adjusting the apperture of the orifice whereby to alter the velocity of the oxygen through the orifice and to vary the ratio of air combined with the oxygen, and supplying the combination of air and oxygen to the mask.

For preference the oxygen is supplied to the chamber at a flow rate of greater than two liters per minute and preferably from 4 to 6 liters per minute, air is admitted to the chamber through apertures of fixed dimension and the velocity of the oxygen flow into the chamber is adjusted by adjusting the cross-sectional area of the orifice through which oxygen is admitted to the chamber to produce dilutions of from 24 to 50%. For preference also the oxygen flow velocity at the orifice is not adjusted continuously but is adjusted in steps each corresponding to an incremental enrichment or dilution.

According to a second aspect the invention consists in gas dilution apparatus comprising:
a chamber having an air inlet and having an outlet adapted for communication with an inhalation mask,
means defining an orifice for admitting oxygen to the chamber,
and means for altering the cross-sectional area of said orifice whereby to alter the velocity of oxygen upon entry to the chamber.

According to a preferred embodiment, the air is admitted to the chamber via one or more windows of predetermined aperture. The cross sectional area of the oxygen admission orifice is controlled by insertion in or withdrawal from the orifice of a stem of smaller diameter than the orifice, the stem increasing in diameter in the axial direction. For preference also the stem diameter changes in a stepwise manner and the depth of insertion of the stem is screw thread controlled.

An embodiment of the invention will now more particularly be described by way of example only and with reference to accompanying drawings wherein:

FIG. 1 is a view of the assembled embodiment in side elevation, and

FIG. 2 is a cross-section of the assembled embodiment of FIG. 1 taken on a plane through the axis.

Figure 5:
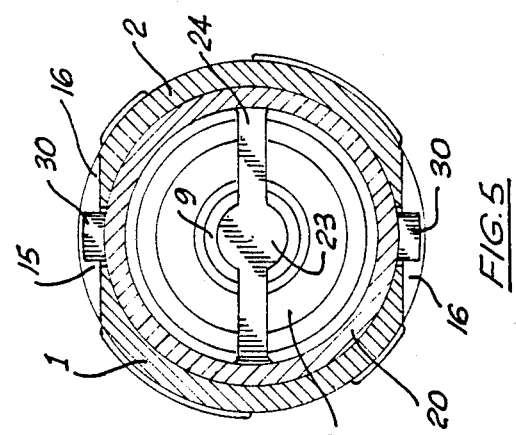
FIG. 5 is a cross-section of the assembled embodiment taken on line 5—5 of FIG. 2.
Figure 4:
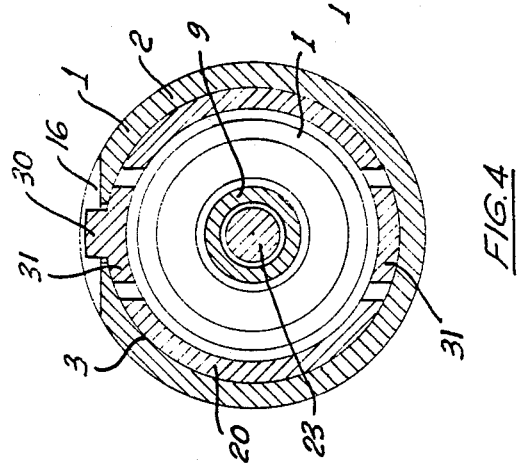
FIG. 4 is a cross-section of the assembled embodiment taken on line 4—4 of FIG. 2.
Figure 3:
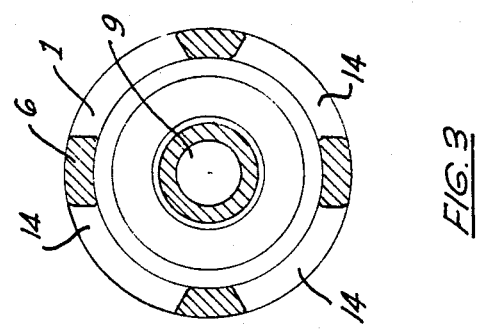
FIG. 3 is a cross-section of the assembled embodiment taken on line 3—3 of FIG. 2.

The drawings are not to the same scale.

With reference to the drawings there is shown an assembly comprising a first barrel part indicated generally at 1 and second barrel or a regulator part 20.

Barrel 1 has a tubular body having a side wall 2 with a cylindrical interior surface 3 and an open outlet end 4. Tubular body 1 reduces in diameter at a shoulder 5 spaced from outlet end 4 to form a manifold chamber defined by a sidewall 6 having a cylindrical interior surface 7 and closed by an end wall 8.

A plurality of equiradially spaced apertures 14 pierce sidewall 6 for admitting air into the manifold chamber.

In the example under description there are 4 apertures 14 having an area in aggregate of 300 sq.mm.

A rigid hollow inlet tube 9 extends concentrically from an upstream end 10 outside the manifold chamber through end wall 8 and to a downstream end 11 in body 2 of barrel 1.

Inlet tube 9 is for preference provided adjacent the upstream end with external tapered barbs 12 of the kind used to retain a push fit flexible tube and in use is connected to an oxygen supply.

Optionally, additional apertures 14A may also be provided in the barrel side wall.

Regulator 20 has a generally tubular side wall 21, an outside diameter which is a snug fit with the interior wall surface 3 of barrel 1 and is provided with a screw thread formation 22 which inter-engages with a thread 17 cut into the interior surface 3 of barrel side wall 2. Interengaging screw formations 22, 17 give an axial movement of about 7 mm per revolution of regulator 20 with respect to barrel 1.

Regulator 20 is adapted at its downstream end 26 for push fit connection to the inlet port of a transparent plastic respirator mask (not shown in the drawings).

A valve stem 23 is mounted axially within regulator 20 by means of a radially extending spider or arms 24.

Stem 23 is stepped in diameter having its least diameter D1 adjacent upstream tip 25 and progressively increasing in diameter D2, D3, D4, D5, D6 in the downstream direction. Preferably the interior diameter of D1 is 2.5 mm, D2 is 2.8 mm, D3 is 3.2 mm, D4 is 3.5 mm and D5 is 3.7 mm, and D6 is 4 mm.

Either stem 23 or the interior of inlet tube 9 or both may if desired have tapered surfaces. Stem 23 is positioned so that each screwed half revolution of regulator 20 relative to barrel 1 inserts or withdraws the stem 23 from tube 9 by an amount which alters the diameter of the gap between the stem external diameter and the internal diameter of tube 9. Thus in use the oxygen admission orifice may be adjusted in area with consequent alteration to oxygen velocity for a given flow rate measured for example in liters per minute.

Barrel 1 has two elongate slots 15 extending parallel to the axis and on diametrically opposite sides of side wall 2. Slots 15 are formed in the present embodiment by inletting chordal flats 16 on the barrel outer wall in a plane which intersects the interior surface 3 of barrel side wall 2.

Regulator 20 is provided with radially outwardly projecting lugs 30 mounted on resilient tabs 31 formed from a portion of regulator side wall 21. Lugs 30 are compressible in a radial direction to a diameter less than the internal diameter of wall surface 3 but are resiliently biased outwardly by tabs 31 into engagement with the interior surface 3 of barrel 1 or into positive locking engagement with slot 15 of barrel 1.

Adjustment of the air dilution is achieved by pinching lugs 30 together enabling lugs 30 to clear slots 15 and permitting rotation of regulator 20, during which lugs 30 slide against interior surface 3 of barrel wall 2 for a half turn whereupon lugs 30 are urged into re-engagement with slots 15 in a positive manner by resilient tabs 31.

If desired, slots 15 may be provided with raised portions 32 (shown only on FIG. 1) near the slot ends whereby unintentional withdrawal of regulator 20 beyond its operative range is made difficult.

As shown in Table I apparatus according to the invention provides a useful range of air to oxygen mixtures without necessitating interchange of the parts of the apparatus and without change to the flow rate of oxygen. Indeed the dilution appears to be substantially independent of flow rate when the oxygen delivery rate is in the range of 4–8 LPM.

TABLE I

| PERCENTAGE AIR DILUTION AT VARIOUS OXYGEN FLOW RATES | | | |
|---|---|---|---|
| OXYGEN FLOW RATE | 4 LPM | 6 LPM | 8 LPM |
| Setting (1) | 50.5% | 50.0% | 49.0% |
| Setting (2) | 40.5% | 40.0% | 40.0% |
| Setting (3) | 35.0% | 35.5% | 36.0% |
| Setting (4) | 31.5% | 31.0% | 31.0% |
| Setting (5) | 28.0% | 28.5% | 29.0% |
| Setting (6) | 24.0% | 24.0% | 24.5% |

It is believed that by careful selection of appropriate dimensions in a manner determinable by routine testing based on the teaching hereof, other embodiments of the invention will permit a broader range of air/oxygen dilutions to be obtained with a single apparatus.

It will be understood that although a stepped stem 23 is preferred and provides more satisfactory manufacturing tolerances, a tapered stem could be employed. Alternatively, a tapered or step bored inlet tube 9 could be used with a cylindrical stem or a combination of such like co-operating parts may be used. Likewise, other valve arrangements could be employed to alter the oxygen velocity at inlet to the chamber for a predetermined air inlet aperture.

The barrel is desirably calibrated to indicate % dilution at various settings. Other means for stepped setting of the parts and/or for click engagement may be employed.

The apparatus may be made from any suitable materials. The parts of a present prototype are moulded from ABS (regulator) and polypropyrene (barrel).

Preferred embodiments according to the invention provides a simple means of adjusting the oxygen:air ratio.

Because in those embodiments at least a half turn is required to change a setting it is difficult for settings to be made in error and it is extremely unlikely if not impossible, for a setting to be altered as a result of an accidental bump.

Moreover a wide range of desired settings can be obtained with one apparatus without need to change oxygen flow rate setting at a supply regulator or to substitute parts.

Although references have been made throughout to oxygen the apparatus and method could be used for other gases or gas mixtures for instance with oxygen-enriched air.

As will be apparent to those skilled in the art from the teaching hereof, the invention may be embodied in other forms and such are deemed to be within the scope hereof.

I claim:
1. A gas dilution apparatus comprising:
a chamber having an air inlet formed from at least one window having a predetermined aperture, and an outlet adapted for communication with an inhalation mask, said chamber being defined by two barrels that are movable with respect to one another, wherein the first barrel includes an orifice for admitting oxygen to the chamber; and the second barrel includes
an elongated stem having an increasing diameter along its longitudinal axis which is insertable within and withdrawable from said orifice for controlling the amount of oxygen admitted through said orifice, wherein said barrels are provided with mutually engaging threads which cooperate so that rotation of one barrel relative to another causes the movement of said stem into and out of said orifice.

2. The apparatus defined in claim 1, wherein the second of the two barrels is penetrated by a slot and an outwardly biased member is included in the surface of the inner barrel, the slot and biased member being sized such that when they are brought into alignment by the rotation of the barrels with respect to each other, the biased member enters the slot and prevents further rotation.

3. A method for adjusting the air dilution of an oxygen supply for an inhalation mask, said method comprising the steps of a providing a chamber defined by two barrels that are telescopically movable with respect to one another, wherein one of said barrels includes an orifice and the other barrel includes an elongated stem having an increasing diameter along its longitudinal axis, which is insertable within and withdrawable from said orifice, b. admitting oxygen into the chamber through said orifice, c. admitting air into the chamber through an inlet formed from at least one window having a predetermined aperture, d. adjusting only the cross-sectional area of the orifice through which oxygen is admitted to the chamber to alter the velocity of the oxygen through the orifice and to vary the ratio of dilution of the oxygen by the air in the chamber, by telescoping the two barrels with respect to each other and moving said elongated stem to insert or withdraw said elongated stem in said orifice, and e. supplying the oxygen diluted by the air to the mask.

4. A method according to claim 3 wherein oxygen is supplied to the chamber at a flow-rate greater than two liters per minute.

5. A method according to claim 4 wherein oxygen is supplied to the chamber at a flow-rate between four and six liters per minute.

6. A method according to claim 3 wherein the velocity of the oxygen flow into the chamber is adjusted by adjusting the cross-sectional area of the orifice through which oxygen is admitted to the chamber.

7. A method according to claim 6 wherein the oxygen dilution varies from 24–50%.

8. A method according to claim 3 wherein the oxygen flow velocity is adjusted in steps each of which corresponds to an incremental enrichment.

9. A method according to claim 3 wherein air is admitted to the chamber through apertures of fixed dimension.

10. A gas dilution apparatus comprising:

a chamber having an air inlet formed from at least one window having a predetermined aperture, and an outlet adapted for communication with an inhalation mask, said chamber being defined by two barrels that are telescopically movable with respect to one another;

wherein one the first barrel includes an orifice for admitting oxygen to the chamber, and the second barrel includes an elongated stem having an increasing diameter along its longitudinal axis which is insertable within and withdrawable from said orifice for controlling the amount of oxygen admitted through said orifice;

wherein telescopic movement of said barrels with respect to each other causes the movement of said stem into and out of said orifice.

11. Gas dilution apparatus of claim 10, wherein said two barrels are telescopically movable with respect to one another by way of a mutually engaging threads which cooperate so that rotation of one barrel relative to the other causes said telescopic movement and the movement of said stem into and out of said orifice.

12. Gas dilution apparatus of claim 11, wherein the second barrel is penetrated by a slot and an outwardly biased member is included in the surface of the first barrel, the slot and biased member being sized such that when they are brought into alignment by the rotation of the barrels with respect to each other, the biased member enters the slot and prevents further rotation.

13. Gas dilution apparatus according to claim 10, wherein the air is admitted to the chamber via a plurality of windows of predetermined aperture.

14. Gas dilution apparatus according to claim 10, wherein the stem diameter changes in a stepwise manner.

* * * * *